United States Patent [19]

Schwartz et al.

[11] Patent Number: 5,321,039
[45] Date of Patent: Jun. 14, 1994

[54] METHOD OF INDUCING A HISTAMINE AGONIST ACTION ON $H_2$ RECEPTORS

[75] Inventors: Jean C. Schwartz; Monique Garbarg, both of Paris; Jean M. Arrang, Gif sur Yvette; Charon R. Ganellin, Grande-Bretagne; Jeanne M. Lecomte, Paris, all of France

[73] Assignees: Societe Civile Bioprojet; Institute National de la Sante et de la Recherche Medicale (INSERM), both of France

[21] Appl. No.: 754,914

[22] Filed: Sep. 6, 1991

Related U.S. Application Data

[63] Continuation-in-part of Ser. No. 684,792, Apr. 15, 1991, abandoned.

[30] Foreign Application Priority Data

Apr. 13, 1990 [FR] France ................... 90 04861

[51] Int. Cl.$^5$ ............... A61K 31/415; C07D 233/54; C07D 233/66; C07D 233/88
[52] U.S. Cl. .................... 514/400; 548/326.1
[58] Field of Search ............ 548/342; 514/400; 542/336.1

[56] References Cited

U.S. PATENT DOCUMENTS

| 3,759,944 | 9/1973 | Black et al. | 548/342 |
| 3,818,097 | 6/1974 | Black et al. | 514/400 |
| 3,891,764 | 6/1975 | Black et al. | 514/400 |
| 3,954,982 | 5/1976 | Black et al. | 514/352 |
| 5,047,418 | 9/1991 | Howson | 514/826 |

FOREIGN PATENT DOCUMENTS

| 0420396 | 4/1991 | European Pat. Off. . |
| 2052692 | 5/1971 | Fed. Rep. of Germany . |
| 1296544 | 11/1972 | United Kingdom . |

OTHER PUBLICATIONS

Agents and Actions, vol. 18, 1/2 (1986), pp. 137–140.
Arch. Pharm., 319 Band, Dec. (1986) Heft 12, pp. 1057–1064.
Medicinal Chemistry, Chap. 6, (1985) pp. 93–118.
Journal of Medicinal Chemistry, vol. 24, No. 8, (Aug. 1981) pp. 913–920.
Van der Werf, et al., *Trends in Pharmacological Sciences,* vol. 10, No. 4, pp. 159–182, Apr. 1989.

*Primary Examiner*—Floyd D. Higel
*Attorney, Agent, or Firm*—Larson and Taylor

[57] ABSTRACT

The invention claims as drugs which are active as agonists of the histamine $H_3$ receptor, the O-[2-(4(5-imidazolyl)-ethyl] isothiourea, 4-(4(5)-imidazolyl) butyramidine and S-[2-(4(5)-imidazolyl)-ethyl] isourea as well as their N-methyl derivatives, these compounds being useful for the preparation of drugs to be used as hypnotic, sleep-inducer, tranquillizer, sedative, anxiolytic, anti-asthmatic and anti-inflammatory agents, notably for the bronchi, the skin or the eyes, or as antigastric ulcer agents.

9 Claims, No Drawings

METHOD OF INDUCING A HISTAMINE AGONIST ACTION ON H₂ RECEPTORS

This application is a continuation-in-part of copending application Ser. No. 07/684,792, now abandoned, filed Apr. 15, 1991.

This invention relates to the therapeutic use of histamine derivatives, a new histamine derivative and the use of these derivatives for the preparation of drugs.

S-[2-(4(5)-imidazolyl)-ethyl] isothiourea (Compound I) has already been described in British Patent GB-A-1,296,544, in which it is described as an antagonist of the effects of histamine, notably on gastric secretion, in animal tests. This compound inhibits the secretion of gastric acid which is stimulated by histamine in anaesthetized rat stomachs under perfusion, in doses between 8 and 256 micromoles per kilogram.

According to C. R. Ganellin (J. Med. Chem., 1981, 24, 913, and Medicinal Chemistry, Chapter 6, p 93–118, Academic Press Inc., London, 1985) this compound at high doses opposes the action of histamine on rat gastric secretion: the 50% inhibiting dose is about 200 μmoles/kg. According to this author Compound I is not a powerful enough histamineantagonist and one must therefore look for a more active agent.

Moreover Sterk et al. (Agents and Actions, 1986, 18, 137 and Arch. Pharm., 1986, 319, 624) have described this Compound I as a partial (50%) agonist of the histamine $H_2$ receptor which it only stimulates at a very high concentration (about 0.1 mM).

These properties as a partial and rather weak $H_2$-agonist suggested that the compound was not therapeutically applicable, considering notably the high doses it would have been necessary to administer, which led one to consider this compound as inefficient and to disregard it for any detailed pharmacological study.

In 1983 Arrang et al. (Nature, 1983, 302, 832) detected the existence of a third histamine receptor called $H_3$.

Applicants have now surprisingly discovered that this Compound I is a full histamine agonist on the $H_3$ receptor which it stimulates at about 1 nanomolar concentration, or about 100,000 times lower than is necessary for an engagement of the $H_2$ receptor. This unexpected property was shown by the inhibiting effect the compound exerts on the liberation and synthesis of endogenous histamine from depolarized brain sections (after the technique described by Arrang et. al., Nature, 1983, 302, 832). From this point of view this compound is 62 times more powerful than histamine and is the most powerful $H_3$ agonist known to this date.

What is more, this compound adequately crosses the blood-brain barrier considering that at an oral dose of 3 mg/kg it produces a maximum inhibition of histamine synthesis in the brain of rats (as measured according to the method of Arrang et al., Nature, 1987, 327, 117). In the same manner it inhibits at a very low dose the synthesis of histamine in several peripheral organs such as the lungs.

Applicants have also established that the corresponding N-methylated derivative (Compound II) having formula

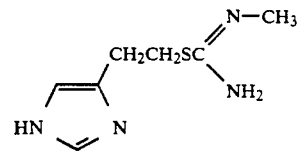

also behaves as a full and comparatively powerful ($EC_{50}=10$ nM) $H_3$ agonist which is also active in vivo. Compound II is about 6 times more powerful than histamine.

European patent application EP-A-0 420 396, published after the priority date of the parent application teaches also that S-[2-(4(5)-imidazolyl) ethyl] isothiourea (Compound I) and 4-(4(5)-imidazolyl) butyramidine (Compound III) are highly potent selective histamine $H_3$-agonists and provides use of these compounds for treating allergic disease and gastrointestinal motility disorders.

Although it was believed, as a theoretical knowledge, that agonists of the $H_3$-receptor of histamine may inhibit the synthesis and release of neurotransmitters such as histamine in the central nervous system, no individual $H_3$-agonist was ever used for such central indication.

Further it was not apparent that the known Compounds I and III may cross the blood-brain barrier and be active in the brain. Also compounds having chemical structures close to those of Compounds I and III were known to be unable to cross the blood-brain barrier.

The object of the invention is a drug having a histamine $H_3$ receptor agonist action, comprising S-[2-(4(5)-imidazolyl)-ethyl] isothiourea (Compound I) or its N-methyl derivative (Compound II).

The object of the invention is a drug which is active as a histamine $H_3$ receptor agonist, including Compound I which is active at a dose between about 0.1 and 10 mg/kg, notably between 0.3 and 3 mg/kg, preferably about 1 mg/kg, by the oral or parenteral route.

The drug may also contain the compound at a concentration between 1 and 100 nanomole/l for topical application to the skin or to the eye, or by air spray, as introduced in an appropriate vehicle.

The object of the invention is also the use of this Compound I for the preparation of a drug to be used as a tranquillizer, sleep-inducer, hypnotic, sedative, anxiolytic, anti-asthmatic and anti-inflamatory agent, notably for the bronchi, the skin or the eyes, or as an anti-gastric ulcer agent. This drug I is notably active at a dose between about 0.1 and 10 mg/kg, notably between 0.3 and 3 mg/kg, preferably 1 mg/kg.

A preferred oral dosage unit for a hypnotic, sleep-inducing, tranquillizer, sedative or anxiolytic drug, comprises, in an usual suitable form, from 5 or 6 mg to 50 or 60 mg of the Compound I.

Another object of the invention is Compound II having the above-given structural formula.

The object of the invention is also a drug which is a histamine $H_3$ receptor agonist, comprising Compound II. This is notably active at a dose between about 1 and 50 mg/kg, notably between 3 and 30 mg/kg, preferably 10 mg/kg.

The drug may also contain the latter compound at a concentration between 10 nanomoles/l and 1 micromole/l for topical application to the skin or the eye or as an air spray, in an appropriate vehicle.

Another object of the invention is also the use of Compound II for the preparation of a drug to be used as an hypnotic, sleep-inducer, tranquillizer, sedative, anxiolytic, anti-asthmatic and anti-inflammatory agent, notably for the bronchi, the skin or the eyes, or as an anti-gastric ulcer agent. This drug is notably active at a dose between about 1 and 50 mg/kg, notably between 3 and 30 mg/kg, and preferably 10 mg/kg.

A preferred oral dosage unit for a hypnotic, sleep-inducing, tranquillizer, sedative or anxiolytic drug, comprises, in an usual suitable form, from 50 or 60 mg to 600 mg of the Compound II.

Another object of the invention is also a drug which is an hypnotic, sleep-inducing, tranquillizer, sedative or anxiolytic agent, containing 4-(4(5)-imidazolyl) butyramidine (Compound III) having formula

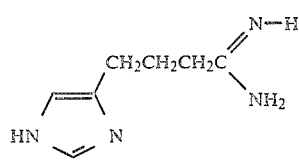

or its N-methyl derivative (Compound IV). The Compound IV, which is N-methyl-4[4(5)-imidazolyl] butyramidine, may be prepared from the nitrile of formula

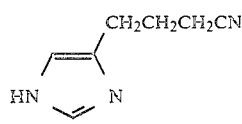

Treatment of the nitrile under anhydrous conditions in the presence of a strong acid (which may be introduced in gaseous form into the reaction mixture) with an alcohol ROH e.g. methanol or ethanol gives an imino-ether of following formula,

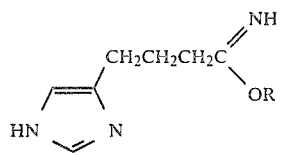

wherein R is, for example, methyl or ethyl, which may be treated with methylamine to yield the required amidine.

Alternatively, treatment of the nitrile at elevated temperature with a methylammonium salt gives the required amidine compound directly.

Another object of the invention is the use of Compounds III or IV for the preparation of said hypnotic, sleep-inducing, tranquillizer, sedative or anxiolytic drug.

Another object of the invention is a drug having an histamine $H_3$ receptor agonist action, comprising O-[2-(4(5)-imidazolyl)ethyl] isourea (compound V) having formula

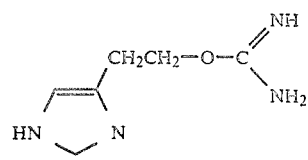

or its N-methyl derivative (Compound VI).

Still another object of the invention is a drug which is an hypnotic, sleep-inducing, tranquillizer, sedative, anxiolytic, anti-asthmatic and anti-inflammatory agent, notably for the bronchi, the skin or the eye or as an anti-gastric ulcer agent containing Compounds V or VI.

Another object of the invention are Compounds V or VI.

Compound V or VI of formula

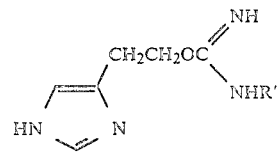

wherein R'=H or methyl may be prepared by treating cyanamide ($H_2NCN$) or methyl cyanamide ($CH_3$—HNCN) with a hydrohalide salt of the compound 2-[4(5)-imidazolyl] ethan-1-ol (formula hereunder) under anhydrous acidic conditions.

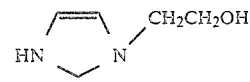

Another object of the invention is the use of compounds V or VI for the preparation of said hypnotic, sleep-inducing, tranquillizer, sedative or anxiolytic drug or for the preparation of an anti-asthmatic or an anti-inflammatory drug notably for the bronchi, the skin or the eyes, or an anti-gastric ulcer drug.

These drugs are notably active at a dose between about 0.1 and 30 mg/kg.

A preferred dosage unit for an hypnotic, sleep-inducer, tranquillizer, sedative or anxiolytic drug comprises, in an usual suitable form, from 5 or 6 mg to 500 or 600 mg of Compounds III, IV, V or VI, where a dosage from 5 or 6 mg to 50 or 60 mg is more preferred for Compounds III or V.

Compounds I to VI may be administered to man in association with a pharmaceutically acceptable excipient or vehicles, as a tranquillizer, sleep-inducer, hypnotic, sedative or anxiolytic agent.

Compounds I and II may notably be prepared by the process as described in British Patent GB-A-1,296,544 or similar methods.

For the preparation of the inventive drugs the compound, once dosed, is mixed with excipients and vehicules as commonly used for the intended oral, parenteral or topical administration.

Of course the above definitions of components I to VI encompass obvious equivalents such as their pharmaceutically acceptable salts.

We claim:

1. A method of inducing a histamine agonist action on $H_3$ receptors of a subject, comprising the step of administering to said subject S-[2-(4(5)-imidazolyl)-ethyl] isothiourea in an amount sufficient to induce said action.

2. The method according to claim 1, wherein the compound S-[2-(4(5)-imidazolyl)-ethyl] isothiourea is administered to said subject at a dosage of between 0.1 and 10 mg/kg.

3. A method of inducing a hypnotic, sleep-inducing, tranquilizing, sedative or anxiolytic action in a subject, comprising the step of administering to said subject S-[2-(4(5)-imidazolyl)-ethyl] isothiourea in an amount sufficient to induce said action.

4. The method according to claim 3, wherein the compound S-[2-(4(5)-imidazolyl)-ethyl] isothiourea is administered to said subject at a unit dosage of 5 to 60 mg.

5. A method of inducing a histamine agonist action on $H_3$ receptors of a subject, comprising the step of administering to said subject the N-methyl derivative of S-[2-(4(5)-imidazolyl)-ethyl] isothiourea in an amount sufficient to induce said action.

6. The method according to claim 5, wherein the N-methyl derivative of S-[2-(4(5)-imidazolyl)-ethyl] isothiourea is administered to said subject at a dosage between 1 and 50 mg/kg.

7. A method of inducing a hypnotic, sleep-inducing, tranquilizing, sedative or anxiolytic action in a subject, comprising the step of administering to said subject the N-methyl derivative of S-[2-(4(5)-imidazolyl)-ethyl] isothiourea.

8. The method according to claim 7, wherein the N-methyl derivative of S-[2-(4(5)-imidazolyl)-ethyl] isothiourea is administered to said subject at a unit dose of 50 to 600 mg.

9. A pharmaceutical composition having a hypnotic, sleep-inducing, tranquilizing, sedative, anxiolytic, anti-inflammatory or anti-gastric ulcer activity, comprising as active principle 0-[2-(4(5)-imidazolyl)-ethyl] isourea or its N-methyl derivative in an amount sufficient to induce said activity in a subject, and a pharmaceutically acceptable excipient or vehicle.

* * * * *

UNITED STATES PATENT AND TRADEMARK OFFICE
CERTIFICATE OF CORRECTION

PATENT NO. : 5,321,039

DATED : June 14, 1994

INVENTOR(S) : SCHWARTZ et al.

It is certified that error appears in the above-indentified patent and that said Letters Patent is hereby corrected as shown below:

On the Title Page, item [54] and column 1, line 3, change "$H_2$" to --$H_3$--.

Signed and Sealed this

Seventeenth Day of January, 1995

Attest:

BRUCE LEHMAN

*Attesting Officer*   *Commissioner of Patents and Trademarks*